United States Patent [19]

Ogawa et al.

[11] Patent Number: 5,362,917
[45] Date of Patent: Nov. 8, 1994

[54] METHOD OF CONTROLLING A HYDROFORMYLATION REACTION

[75] Inventors: Morimasa Ogawa; Genichi Emoto; Akio Ueda; Takao Kibayashi; Keitaro Nakata; Tsuneo Inoue, all of Kurashiki, Japan

[73] Assignee: Mitsubishi Kasei Corporation, Tokyo, Japan

[21] Appl. No.: 125,795

[22] Filed: Sep. 24, 1993

[30] Foreign Application Priority Data

Sep. 25, 1992 [JP] Japan .................. 4-279301
Sep. 13, 1993 [JP] Japan .................. 5-251108
Sep. 13, 1993 [JP] Japan .................. 5-251109

[51] Int. Cl.$^5$ ......................... C07C 45/50
[52] U.S. Cl. ................... 568/454; 568/451; 568/452; 568/453
[58] Field of Search ............... 568/453, 452, 451, 454

[56] References Cited

U.S. PATENT DOCUMENTS 4,593,126 6/1986 Cornils et al. ............... 568/454
5,053,551 10/1991 Harrison et al. ............... 568/454

FOREIGN PATENT DOCUMENTS 1527234 12/1989 U.S.S.R. .
1555323A1 4/1990 U.S.S.R. .

*Primary Examiner*—Werren B. Lone
*Attorney, Agent, or Firm*—Oblon, Spivak, McClelland, Maier & Neustadt

[57] ABSTRACT

A method for controlling a hydroformylation reaction for producing an aldehyde by subjecting an olefin, a feed oxo gas containing hydrogen and carbon monoxide, and a recycled gas withdrawn from a reactor and returned to the reactor, to a hydroformylation reaction in the reactor in the presence of a catalyst, which comprises:

setting out a target value for the partial pressure of carbon monoxide in the reaction system to control the hydroformylation reaction;

detecting the partial pressure of carbon monoxide corresponding to the target value; and comparing the detected partial pressure of carbon monoxide with the target value to adjust a flow rate of a discharged gas from the reactor; or comparing the detected partial pressure of carbon monoxide with the target value to adjust a flow rate of the feed oxo gas.

20 Claims, 13 Drawing Sheets

21: CO CONCENTRATION TARGET VALUE
22: FEED OXO GAS FLOW RATE
23: PURGE GAS FLOW RATE
24: CO CONCENTRATION DETECTED VALUE

METHOD OF CONTROLLING A HYDROFORMYLATION REACTION

The present invention relates to a method of controlling production ratio of normal aldehyde and isoaldehyde of a formed product by controlling the partial pressure of CO in a reaction system, in a hydroformylation reaction wherein an oxo gas containing hydrogen and carbon monoxide (CO) and an olefin.

A process has conventionally been adopted wherein an aldehyde containing normal aldehyde and isoaldehyde is formed by a hydroformylation reaction of which raw material is an oxo gas and an olefin. In this process, a method has been known wherein the production ratios of normal aldehyde and isoaldehyde (hereinafter production ratio of aldehyde) is controlled to desired values, by controlling the partial pressure of CO in a recycled gas by adjusting the partial pressure (concentration) of CO in the oxo gas.

FIG. 1 shows a system diagram as an outline diagram of a general process wherein the hydroformylation reaction is performed. In FIG. 1, the system is provided with a hydroformylation reactor 1 and a gas/liquid separator 2. The reactor 1 is supplied with raw materials and a catalyst respectively from an olefin supply line 11, an oxo gas supply line 12 and a catalyst supply line 14. A gaseous recycled gas separated at the gas/liquid separator 2 is again returned to the reactor 1 through a recycled gas supply line 13, and an aldehyde is produced by reaction with an olefin which is a raw material. The produced aldehyde is withdrawn from an aldehyde product withdrawing line 15. A discharge control valve 9 which is set to prevent the accumulation of inert gas components such as methane, is intermittently operated to purge a portion of the recycled gas.

A target value of the partial pressure of CO in the recycled gas is provided in correlation to a desired production ratio of aldehyde. A control of the partial pressure of CO in the oxo gas which is a raw material is performed for controlling the partial pressure of CO in the recycled gas based on the target value. A control of a supplied feed hydrogen rate is performed by, for instance, a PID (proportion, integration and differentiation) control device, since the control of the partial pressure of CO is possible by adjusting the feed hydrogen rate which is introduced into the oxo gas through a hydrogen supply line 16.

The production ratio of aldehyde is often changed in accordance with the demand of product. In such a case, the target value of the partial pressure of CO in the recycled gas is newly determined based on the new production ratio of aldehyde. The feed hydrogen rate is newly determined based on the target value, and the determined feed hydrogen rate is used as a set value for the PID controller. Normally, the setting out of the target value of the partial pressure of CO is carried out by an operator, and thereafter, the feed hydrogen amount is PID-controlled such that the rate agrees with the set value, based on the target value.

Further, a method is disclosed in a Soviet Patent SU1555323, wherein the yield of n-butyl aldehyde is promoted by changing ratios of hydrogen and carbon monoxide in an oxo gas entering into a reactor, in accordance with carbon monoxide in a gas effluented from the reactor, with respect to a method of controlling an one-path type hydroformylation process of propylene which is different from the above-mentioned gas recycled type process.

In the above Soviet patent, a ratio of $H_2/CO$ in the supplied oxo gas is changed by controlling a flow rate of a gas adding to the oxo gas, whose major component is carbon monoxide.

There have been following problems in the conventional method of controlling a hydroformylation reaction wherein the feed hydrogen amount is controlled, or in the method of the Soviet patent SU1555323 wherein the feed carbon monoxide amount is controlled.

① The time constant of the process is large in the hydroformylation reaction, and the partial pressure of CO in the recycled gas significantly fluctuates by the change of the composition of the feed gas. Accordingly, it is necessary to change the set value in many stages, when the set value of the feed hydrogen amount or feed carbon monoxide amount is determined, which is a burden for the operator.

② Due to the above reason, there causes an individual difference in the operational results depending on the skill of the operator, in changing the set value of the feed hydrogen amount or the feed carbon monoxide amount, and the process is apt to be unstable when the set value is changed.

③ The control of the partial pressure of CO becomes especially unstable when the production amount per unit time (production rate) of aldehyde is changed, since the process characteristic is changed.

④ In case wherein much of components other than hydrogen and carbon monoxide are contained in the raw material gas, for instance, when the partial pressures of olefin (propylene), paraffin (propane) or other inert gas are elevated, it is difficult to control the partial pressure of CO in the recycled gas in a desired range, only through the control of the feed hydrogen amount or the feed carbon monoxide amount.

In view of the problems in the conventional method of controlling a hydroformylation reaction, it is an object of the present invention to provide a method of controlling a hydroformylation reaction wherein the control of the partial pressure of CO in the reactor is facilitated, and accordingly, the production ratio of aldehyde can easily be controlled to a desired value.

According to an aspect of the present invention, there is provided a method for controlling a hydroformylation reaction for producing an aldehyde by subjecting an olefin, a feed oxo gas containing hydrogen and carbon monoxide, and a recycled gas withdrawn from the reactor and returned to the reactor, to a hydroformylation reaction in the reactor in the presence of a catalyst, which comprises:

setting out a target value for the partial pressure of carbon monoxide in the reaction system to control the hydroformylation reaction;

detecting the partial pressure of carbon monoxide corresponding to the target value; and comparing the detected partial pressure of carbon monoxide with the target value to adjust a flow rate of a discharged gas discharged from the recycled gas; or comparing the detected partial pressure of carbon monoxide with the target value to adjust a flow rate of the feed oxo gas.

It is possible to produce aldehyde in a desired production ratio under this construction. It is possible to prevent the concentration of CO in the reactor from significantly fluctuating, when the target value of the partial pressure of CO is changed, by adopting the above construction.

In a preferable embodiment of this invention, the detection of carbon monoxide is performed by detecting the partial pressure of carbon monoxide in the recycled gas which is returned to the reactor.

Further, in another preferable embodiment, the detection of the partial pressure of carbon monoxide is performed by detecting the partial pressure of carbon monoxide of the oxo gas wherein the recycled gas which is returned to the reactor joins with the feed oxo gas which is supplied to the reactor.

According to another aspect of the present invention, there is provided a method for controlling a hydroformylation reaction according to the former aspect further comprising:

storing in a computer a process model for simulating the hydroformylation reaction which is provided with a predetermined signal transfer function having an input of the operational amount to adjust the flow rate of the discharged gas or the feed oxo gas and an output of a calculated value of the partial pressure of carbon monoxide;

providing the process model with the input by successively selecting an input series comprising a plurality of inputs which are successively generated at every predetermined cycle;

successively calculating a future output series based on the output of the process model;

selecting an output series among the calculated future output series wherein a difference between the future output series and the predetermined future target value is small; and setting out the operational amount based on the input series corresponding to the selected one of the output series.

In a preferable embodiment, the selection one of the output series from some output series is performed, for instance, in accordance with the method of least squares.

According to the above preferable embodiments, a stable control of process can be performed irrespective of the skill of an operator for operating the change.

In the above preferable embodiments, the signals relating to the flow rate and the composition of gas to be discharged are detected, the coefficient of the signal transfer function can be provided based on at least the signals relating to the flow rate and the composition of the discharged gas. By adopting such a constitution, a large variation of the partial pressure of CO in the reactor can be restrained and a stable control is made possible.

Further, in the present invention, the signals concerning the flow rate and the composition of the feed oxo gas are further detected, and the operational amount is determined further based on the signals relating to the detected flow rate and composition. By adopting this construction, the concentration of CO can be controlled in a desired range, irrespective of a large variation of the composition of the feed oxo gas.

Figure 1:
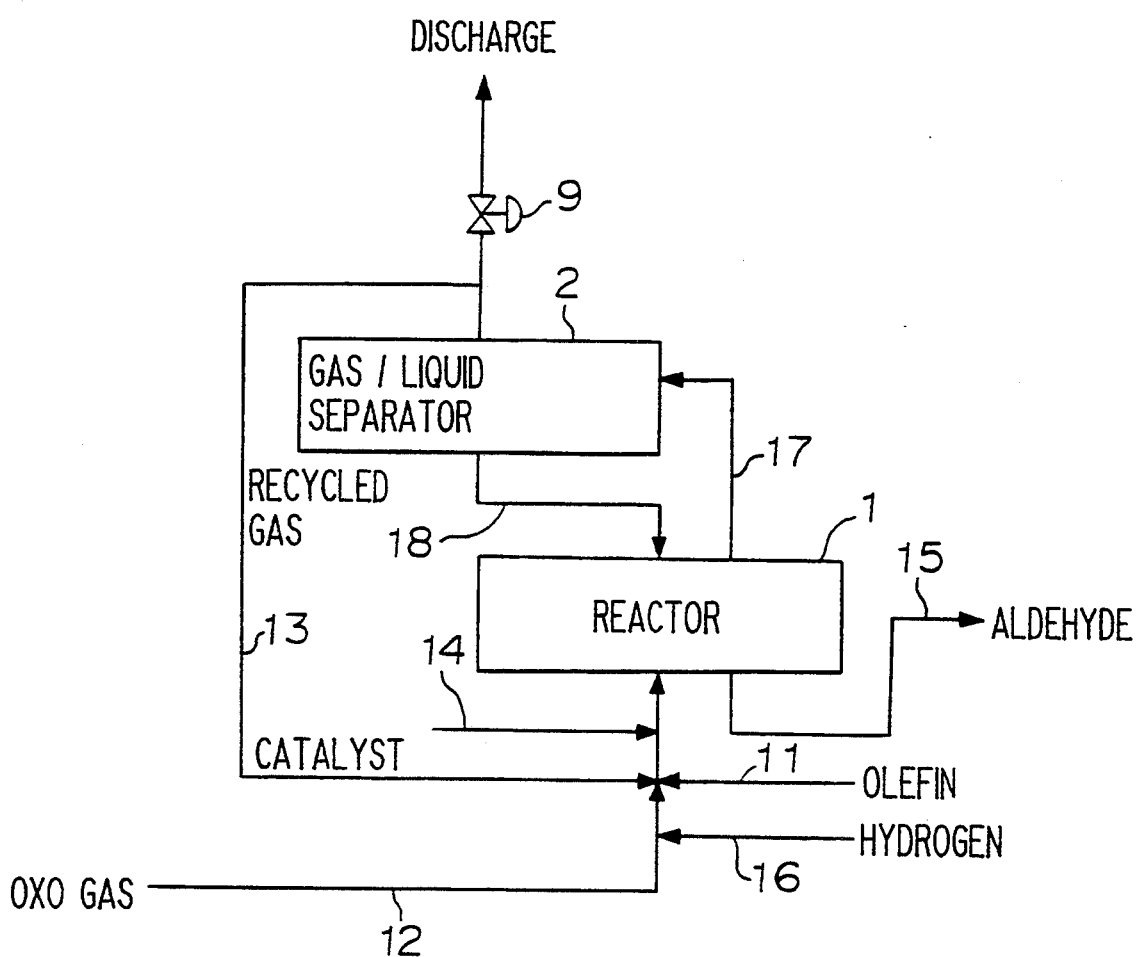
FIG. 1 is a system diagram showing a construction of a system performing a control method of a hydroformylation reaction in the conventional example and the first embodiment of this invention.

In this invention, the olefin which is used as a raw material of a hydroformylation reaction is not particularly restricted, so far as it is an organic compound provided at least with one olefinic double bond in the molecule. For instance, ethylene, propylene, butene, butadiene, pentene, hexene, hexadiene, octene, octadiene, decene, hexadecene, octadecene and the like are pointed out.

In this invention, as a catalyst, a Group VIII metal complex, or a complex soluble in a solution containing an organic compound which includes at least one metal selected from the group consisting of iron, cobalt, nickel, ruthenium, rhodium, palladium, osmium, iridium and platinum, and further includes a ligand such as an organophosphorus compound, for instance, a phosphine such as triarylphosphine or a phosphate or the like.

It is not indispensable to use a solvent for reaction in performing a hydroformylation reaction. However, if necessary, it is possible to use a solvent inert to the hydroformylation reaction. As preferable specific examples of solvents, an aromatic hydrocarbon compound such as toluene, xylene or dodecylbenzene and the like, ketones such as acetone, diethyl ketone, methyl ethyl ketone, ethers such as tetrahydrofuran, dioxane and the like, esters such as ethyl acetate, di-n-octylphthalate and the like, are pointed out.

As a mixture gas of hydrogen and carbon monoxide subjected to the reaction, an oxo gas or a water gas is used. In this specification, these are summerizingly called "oxo gas".

As the reaction condition of the hydroformylation reaction process, conventionally adopted conditions can be used. For instance, the reaction temperature is selected in a range of room temperature through 200° C., preferably 50° C. through 150° C. The reaction pressure is selected from a range of an ordinary pressure through 200 atmospheric pressure, preferably 5 through 100 atmospheric pressure, especially preferably, 5 through 50 atmospheric pressure. The molar ratio of hydrogen to carbon monoxide ($H_2/CO$) is normally selected from a range of 10/1 through 1/10, preferably, 1/1 through 6/1. As the reaction system of the hydroformylation reaction, a continuous system which is performed in an agitation type reaction vessel or a bubble tower type reaction vessel, can be adopted. However, it is preferable to use the agitation type reaction vessel.

In this invention, the partial pressure of CO in a reactor which is provided in correlation with a desired production ratio of an aldehyde which is the reaction product, is set as, for instance, a target value in a PID control system, and the partial pressure of CO in the reactor is controlled to the target value, by controlling the discharged flow rate of the recycled gas withdrawn from the reactor or the flow rate of the feed oxo gas which is supplied to the reaction system, based on the setting.

A detailed explanation will further be given to especially preferable embodiments of this invention, as follows. In these embodiments, in controlling the hydroformylation reactor, various methods of firstly, a CO model predictive control, secondly, a process gain scheduling, and thirdly, a feed forward control, are adopted.

1. CO Model Predictive Control

First, before the control, a process model having a predetermined transfer function is stored in a computer for the control. As the process model, for instance, a system of time-lag of first order including a dead time, is adopted. The transfer function $G(s)$ of this model is expressed by the following equation.

$$G(s) = \{K_p/(1+T_p \cdot s)\} \cdot \exp(-T_L \cdot s) \quad (1)$$

where $K_p$ is a process gain, $T_p$, a time constant which is a value provided by a past process response, $T_L$, a dead time which is a value provided by a past process response, and s, a Laplacian operator.

Figure 2:
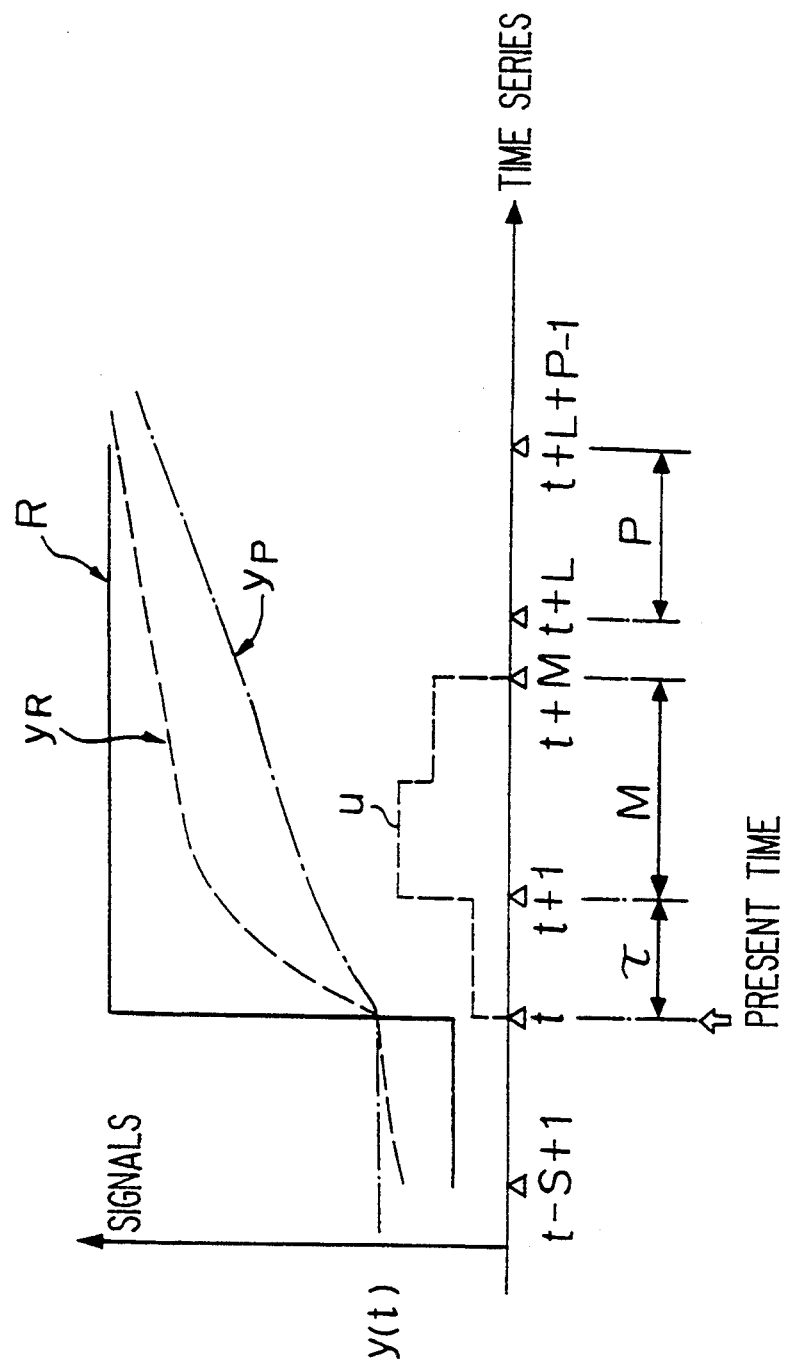
FIG. 2 shows a graph for explaining the control of this invention.

FIG. 2 is a graph for explaining the behavior of control in the CO model prediction control. In FIG. 2, a target value R of the partial pressure of CO at the present time t is stepwisely changed in accordance with the change of the production ratio of aldehyde. The operational amount to adjust the flow rate of the discharged gas or the feed oxo gas which is necessary for the control, is determined by the process model predictive control, based on a deviation of the present partial pressure of CO from the target value of the partial pressure of CO. The procedure is as follows.

Step 1

A reference trajectory $y_R$ having a smoother waveform is calculated from the given target value R of the partial pressure of CO. This is performed for avoiding a situation wherein the system becomes unstable by the rapid change of the target value. An example of the reference trajectory $y_R$ is shown in FIG. 2.

Step 2

An output prediction series (partial pressure of CO of recycled gas) from a future time $t+L\tau$ to a time $t+(L+P)\tau$, is expressed with $\tau$ as a control period, and an input series of an input u (discharged flow rate or a feed oxo gas rate) from the present time t to a time $t+M\tau$ which is exemplified by a broken line, as a parameter. M, P and L are respectively a control horizon of the operational amount, P, a coincidence horizon of an agreement between an output and a target value, and L, a starting time point of the coincidence horizon of an agreement between an output and a target value, which are determined in designing the control system.

When $y_M(t+L)$ is determined to be a model prediction value of the partial pressure of CO at the future time $t+L\tau$ which is directly provided by the process model from one input series, a model prediction series $Y_M$ including the prediction value is expressed as follows.

$$Y_M = [y_M(t+L), \ldots, y_M(t+L+P-1)]^T$$

Further, when $y_P(t+L)$ is determined to an output prediction value at the time $t+L\tau$ which is provided by a correction of the model prediction value $y_M(t+L)$ of the partial pressure of CO, an output prediction series (the partial pressure of CO) $Y_P$ between the future time $t+L\tau$ and the time $t+(L+P-1)\tau$, including the output prediction value, is similarly expressed as follows.

$$y_P = [y_P(t+L), \ldots, y_P(t+L+P-1)]^T$$

A correction term of the process model is provided for obtaining the output prediction series $Y_P$ by correcting the model prediction series $Y_M$. In this case, a difference between an actually measured value y(t) of the partial pressure of CO at the present time t, and the output prediction value $y_M(t)$ at the present time which is provided by the process model from the past data, is determined to be the correction term.

Series Y and $Y_{MO}$ for the above correction are defined as follows.

$$Y = [y(t), \ldots, y(t)]$$

$$Y_{MO} = [[y_M(t), \ldots, y_M(t)]$$

The output prediction series $Y_P$ is expressed as follows by the above definition.

$$Y_P = Y_M + Y - Y_{MO} \quad (2)$$

where there is a following relationship between the model prediction series $Y_M$ and a series $Y_{MO}$ including the output prediction value $y_M(t)$ at the present time.

$$Y_M = Y_{MO} + A_F \cdot \Delta U_M + A_0 \cdot \Delta U_0 \quad (3)$$

The model prediction series $Y_M$ is provided based on the above equation (3). When the model prediction series $Y_M$ is provided, the output prediction series $Y_P$ is provided based on equation (2).

The second term on the right end side of equation (3) is a term for future prediction, and the third term is a term for prediction based on the past data. $A_F$ in the second term is a response series of the prediction model which is expressed as follows.

$$A_F = \begin{bmatrix} a_L, & a_{L-1}, & \ldots, & a_{L-M+1} \\ a_{L+1}, & a_L, & \ldots, & a_{L-M+2} \\ \cdots & \cdots & \cdots & \cdots \\ \cdots & \cdots & \cdots & \cdots \\ \cdots & \cdots & \cdots & \cdots \\ a_{L+P-1}, & a_{L+P-2}, & \ldots, & a_{L-M+P} \end{bmatrix}$$

$a_k$ in the above equation is a step response series determine by the transfer function, which is expressed as follows.

$$a_k = 0 \quad (0 \leq k\tau \leq T_L)$$

$$a_k = K_P\{1 - \exp(-(k\tau - T_L)/T_P)\} \quad (T_L \leq k\tau) \quad (4)$$

$$a_k = a_s \quad (s < k)$$

Further, $\Delta U_M$ in the second term of equation (3), is an input series composed of input parameters from the time t to the time $t+M-1$, that is, a series corresponding to the discharged flow rate of the recycled gas or the flow rate of the feed oxo gas at the respective times during the above time interval. $\Delta U_M$ is expressed as follows by parameters $\Delta u(t)$ to $\Delta u(t+M-1)$ showing the discharged flow rate or the flow rate of the feed oxo gas at the respective time.

$$\Delta U_M = [\Delta u(t), \Delta u(t+1), \ldots, \Delta u(t+M-1)]^T$$

The term for future prediction of equation (3) is calculated by the selection of the respective parameters.

$A_0$ and $\Delta U_0$ in the third term on the right hand side of equation (3) are respectively a process characteristic matrix, and an input series of operational amount, which are expressed as follows.

$$A_0 = \begin{bmatrix} a_{L+1} - a_1, & a_{L+2} - a_2, & \ldots, & a_{L+S-1} - a_{S-1} \\ a_{L+2} - a_1, & a_{L+3} - a_2, & \ldots, & a_{L+S} - a_{S-1} \\ \ldots & \ldots & \ldots & \ldots \\ \ldots & \ldots & \ldots & \ldots \\ \ldots & \ldots & \ldots & \ldots \\ a_{L+P} - a_1, & a_{L+P+1} - a_2, & \ldots, & a_{L+S+P-1} - a_{S-1} \end{bmatrix}$$

$$\Delta U_0 = [\Delta u(t-1), \Delta u(t-2), \ldots, \Delta u(T-s+1)]^T$$

The third term of equation (3) is provided by the above $A_0$ and $\Delta U_0$.

As stated above, the process computer successively selects the input series one by one and successively input them to the process model, by selecting the respective parameters of the input series $\Delta U_M$, in a predetermined order. The correction is performed based on equation (2) with respect to the model prediction series $Y_M$ which is successively provided from the output of the process model, thereby successively providing the output prediction series $Y_P$.

Step 3

An input series is calculated by using the method of least squares, such that a difference between the future output prediction series $Y_P$ which is obtained based on the process model in Step 2, and the values of the reference trajectory $y_R$ which is obtained in Step 1, in a time interval from the future time $t+L\tau$ to the time $t+(L+P)\tau$, is minimized. That is, one output prediction series is selected by the following equation (5), which provides one of the successively calculated output prediction series $Y_P$, which provides the nearest value to the reference trajectory series that is prescribed by the reference trajectory $y_R$.

$$\text{Minimize } ||Y_P - Y_R||^2 \quad (5)$$

where $Y_R$ is the reference trajectory series.

The reference trajectory series $Y_R$ can be provided, for instance, by the following equation from the output at the present time.

$$Y_R = A \cdot F \cdot y(t) + (I - A) \cdot \Gamma$$

where A, $\Gamma$ and F are respectively, A: weight vector, $\Gamma$: a target value vector in a period wherein the agreement between the output and the target value is intended, E: unit matrix, which are expressed by the following equations. In the following equations, $\alpha$ is a parameter and $0 < \alpha < 1$, $\gamma(t)$ is the target value at the time t, and I is a unit matrix.

$$A = [\alpha, \alpha^2, \ldots \alpha^P]^T$$

$$F = \text{diag}[1, 1, \ldots, 1]^T$$

$$\Gamma = [\gamma(t+L), \ldots, \gamma(t+L+P-1)]^T$$

When the one output prediction series $Y_P$ is provided which can provide an output that is the nearest to the future target value, as above, the input series which provides the output prediction series is determined as a series of the operational amount to adjust the flow rate of the discharged gas or the feed oxo gas. The flow rate of the discharged gas or the feed oxo gas is successively selected based on the series of the operational amount.

2. Process Gain Scheduling

When the production rate of the hydroformylation reactor is changed, the characteristic of process changes in accordance thereto, wherein especially the change of the process gain which is the coefficient $K_P$ of the transfer function $G(s)$ of equation 1 is conspicuous. Accordingly, the process gain in the process model of equation (1) is automatically changed, to maintain a stable control, when the production rate is changed. This method is called gain scheduling. In this Example, the gain scheduling is performed, as follows.

When $F_t$ is defined to be a total purging amount of gas which is discharged from the discharge control valve, and $F_{H2}$, $F_{CO}$ and $F_i$, respectively, a flow rate of $H_2$, a flow rate of CO and a flow rate of an inert component in the total discharging rate, the following equation is established.

$$F_t = F_{H2} + F_{CO} + F_i \quad (6)$$

When $A_{CO}$, $A_{H2}$ and $A_i$ are respectively defined to be a concentration of CO, a concentration of $H_2$ and a concentration of the inert component in the discharged gas, the following equation (7) is established from equation (6).

$$A_{CO} = F_{CO}/F_t = F_{CO}/(F_{H2} + F_{CO} + F_i) \quad (7)$$

When $A_{CO}$ is totally differentiated, the following equation (8) is provided.

$$dA_{CO} = \frac{\partial A_{CO}}{\partial F_{H2}} dF_{H2} + \frac{\partial A_{CO}}{\partial F_{CO}} dF_{CO} \quad (8)$$

When equation (8) is substituted by equation (7), the following equation (9) is established.

$$dA_{CO} = 1/F_t\{-(F_{CO}/F_t) \cdot dF_{H2} + (F_{H2}/F_t + F_i/F_t) \cdot dF_{CO}\} \quad (9)$$

Further, the following equations are established by the definition.

$$A_{CO} = F_{CO}/F_t \quad (10)$$

$$A_{H2} = F_{H2}/F_t \quad (11)$$

The following equations (12) and (13) are established in equations (10) and (11) wherein a variation in composition is ignored in comparison with a variation in flow rate, since the composition of raw material gas and the reaction temperature are maintained almost constant, and the reaction is stabilized in a steady state.

$$dF_{H2} = A_{H2} \cdot dF_t \qquad (12)$$

$$dF_{CO} = A_{CO} \cdot dF_t \qquad (13)$$

When equation (9) is substituted by equations (12) and (13), the following equation are established.

$$dA_{CO} = (A_i \cdot A_{CO}/F_t) \cdot dF_4 \qquad (14)$$

Accordingly, $$dA_{CO}/dF_t = A_i \cdot A_{CO}/F_t \qquad (15)$$

The left hand side of equation (15) is the change of the partial pressure of CO with respect to the change of a unit rate of discharging, that is, the process gain $K_P$ defined by equation (1). Accordingly, the following equation is established.

$$K_P = A_i \cdot A_{CO}/F_t \qquad (16)$$

In case wherein the partial pressure of CO in the reactor is controlled by controlling the feed oxo gas flow rate, since the composition of the raw material gas and the reaction temperature remain almost constant and the reaction is stabilized, a reaction rate y remains constant in a steady state, and the following equations are established.

$$P_t = 2y + F_t \qquad (17)$$

where $P_t$ is the feed oxo gas rate.

$$dF_t = 2dP_{H2} \qquad (18)$$

$$dF_t = 2dP_{CO} \qquad (19)$$

where $P_{H2}$ is a flow rate of $H_2$ and $P_{CO}$, a flow rate of CO in the feed oxo gas, since the composition of the raw material oxo gas is as $H_2/CO = 1$. When the equation (9) is substituted by equations (18) and (19), the following equations are established.

$$dA_{CO} = \tfrac{1}{2}F_t(1 - 2A_{CO}) \cdot dF_t \qquad (20)$$

From equation (17), $$dP_t = dF_t \qquad (21)$$

Accordingly, $$dA_{CO}/dP_t = \tfrac{1}{2}F_t(1 - 2A_{CO}) \qquad (22)$$

The left hand side of equation (22) is the change of the partial pressure of CO with respect to the change of a unit rate of feed oxo gas, that is, the process gain $K_P$ defined by equation (1). Accordingly, $K_P$ is expressed by the following equation (23).

$$K_P = \tfrac{1}{2}F_t(1 - 2A_{CO}) \qquad (23)$$

By changing the process gain in accordance with equation (16) or (23), the transfer function accurately expressing the process response can be provided at every occasion of the change.

Accordingly, it is possible to perform the gain scheduling by obtaining the value of $K_P$ in accordance with the equation (16) or (23), by sampling the process data $A_i$, $A_{CO}$ and $F_t$ from detection units at a constant period, and by changing the value of gain $K_P$ of the process model.

3. The Feed Forward Control

The partial pressure of CO in the reactor is influenced by the change of the composition in the feed oxo gas. Therefore, to compensate the variation in the concentration of CO in the feed oxo gas, a feed forward control is performed wherein the discharging flow rate u or the flow rate of the feed oxo gas $F_{in}$ is controlled. When $C_{CO}$ is the partial pressure (concentration) of CO in the recycled gas, and $B_{CO}$, the concentration of CO in the feed oxo gas, the following equations (24) and (25) are established by the mass balance around the reactor.

$$du/dt = (F_{in}/C_{CO}) \cdot dB_{CO}/d_t \qquad (24)$$

$$dF_{in}/dt = -(F_{in}/B_{CO}) \cdot dB_{CO}/d_t \qquad (25)$$

Accordingly, when a variation is caused in the partial pressure of CO, $B_{CO}$ in the feed oxo gas, the variation of CO is compensated by changing the purging flow rate u based on equation (24) or the flow rate of the feed oxo gas $F_{in}$ based on equation (25)

A further detailed explanation will be given of the present invention in reference to the drawings. The control method of the hydroformylation reaction in the first embodiment of this invention, is carried out in the system, for instance, shown by the system diagram of FIG. 1 which has been explained in the conventional technology. A desired value of the partial pressure of CO in the recycled gas is set as the target value in the PID control device. The discharged flow rate of the recycled gas withdrawn from the reactor 1 or the feed oxo gas flow rate which is fed to the reactor 1 is controlled based on the target value and a detected amount of the concentration of CO in the recycled gas supply line 13. The control of the discharged flow rate or the feed oxo gas flow rate is carried out by the control of the degree of opening of the discharge control valve 9 or the feed gas control valve 10, such that the concentration of CO in the recycled gas agrees with the target value.

Figure 3:
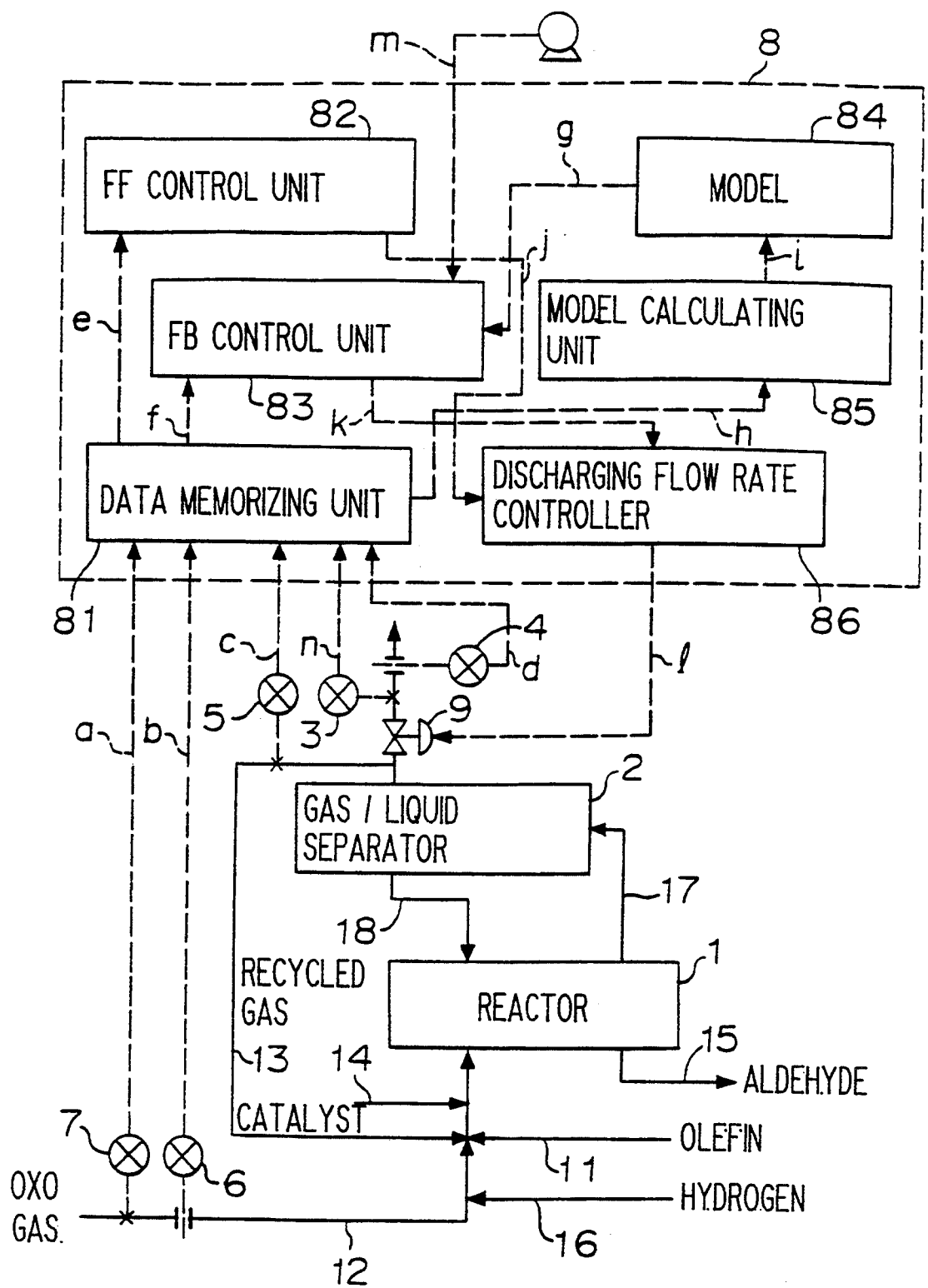
FIGS. 3 and 4 are system diagrams showing the control method of a hydroformylation reaction of the second embodiment of this invention.
Figure 4:
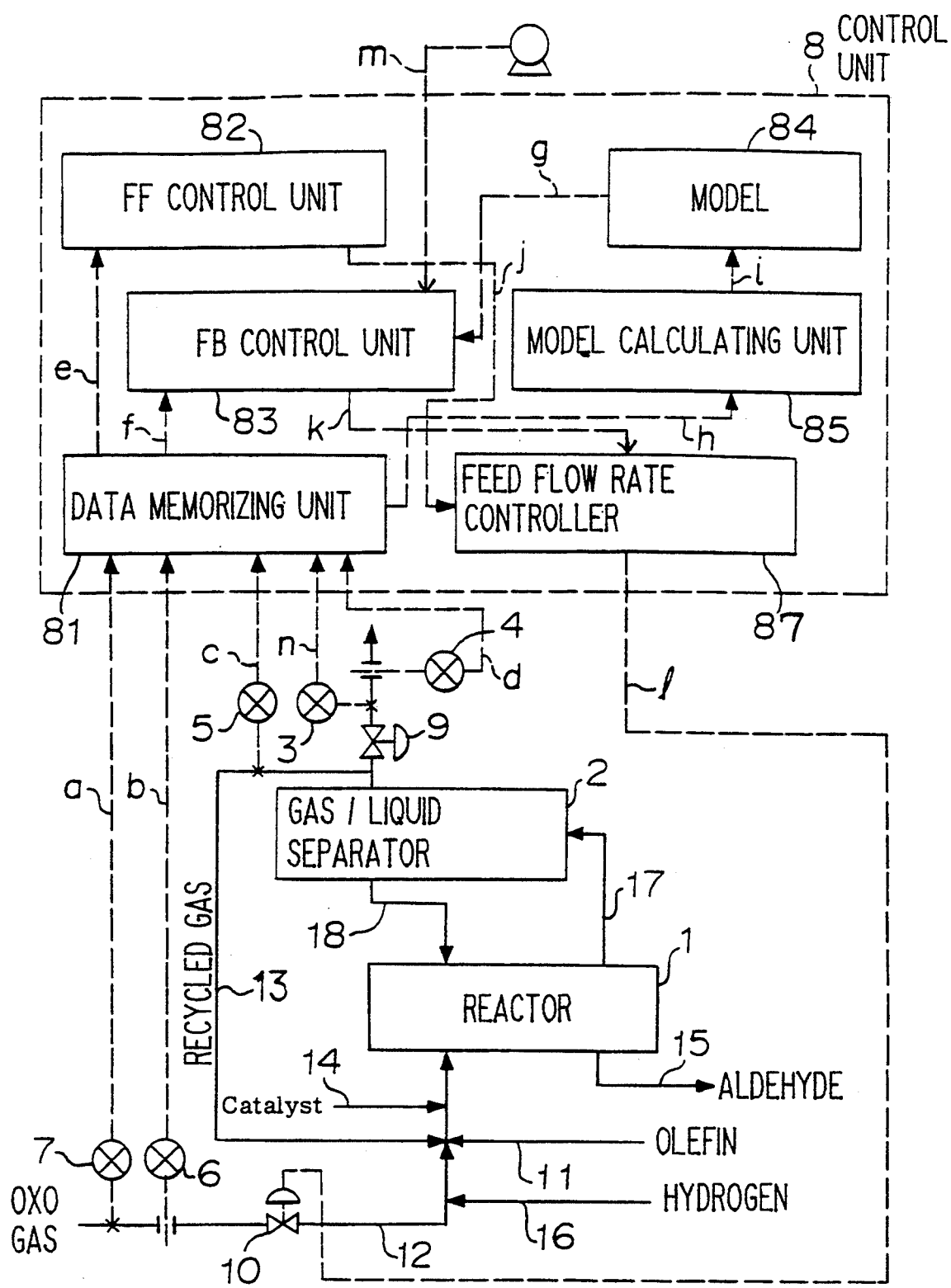

FIGS. 3 and 4 show system diagrams of a system for performing a second embodiment of the control method of a hydroformylation reaction. In FIGS. 3 and 4, this system is provided with a reactor 1, a gas/liquid separator 2, a discharge control valve 9, an oxo gas feed control valve 10, pipings for respective routes and a control unit 8, signal detecting units and operation units are provided at predetermined positions, and are connected to the control unit 8 through wirings for control.

The reactor is connected with an olefin supply line 11, an oxo gas supply line 12 for feeding raw material, and the oxo gas supply line 12 is connected with a hydrogen gas supply line 16. The reactor 1 is further connected with a catalyst supply line 14, an aldehyde product withdrawing line 15 for withdrawing an aldehyde product, connection lines 17 and 18 between the reactor and the gas/liquid separator 2, and a recycled gas supply line 13 for withdrawing the recycled gas from the gas/liquid separator 2 and for returning it to the reactor 1.

A recycled gas discharge control valve 9 is provided on the side of the gas/liquid separator 2 of the recycled gas supply line 13. A discharged gas composition analysis meter 3 and a recycled gas discharge flow rate meter 4 are installed on the exit side of the discharge control valve 9. Further, a CO analysis meter 5 is installed at the recycled gas supply line 13, for analyzing the concentration of CO in the recycled gas which is supplied to the reactor 1. Further, a feed control valve 10 is installed at the oxo gas supply line 12, for controlling a flow rate of the oxo gas which is fed to the reactor 1. The oxo gas supply line 12 is installed with a flow rate meter 6 for detecting a flow rate of oxo gas and a CO analysis meter 7 for measuring the composition of oxo gas.

The control unit 8 is a process computer which controls the hydroformylation reaction system total process, and is functionally composed of a data memorizing unit 81 for memorizing once the detected data from each detecting unit, a feed forward (FF) control unit 82 for compensating the variation of the composition of the feed oxo gas, a feedback (FB) control unit 83 for controlling the concentration of CO in the recycled gas in accordance with the target value, a model calculating unit 85 for calculating the process model, a model 84 wherein the calculated model is stored, and a controller 86 or 87 for controlling the discharged flow rate or the feed oxo gas flow rate. The operator inputs the target value m of the concentration of CO in the recycled gas to the feedback control unit 83 in accordance with the necessity. It is possible that the control unit 8 is constructed as a DCS (distribution type computer system), and it is possible that signals of the respective control units is outputted as control signals of a DDC (direct digital control).

In the system constructed as above, the reactor 1 is continuously supplied with olefin, oxo gas, recycled gas, catalyst and hydrogen gas by supplying them in accordance with the reaction condition, through the respective supply lines 11, 12, 13, 14 and 16. Normal aldehyde and isoaldehyde are produced with desired ratios in the reactor 1, by reacting olefin and oxo gas by a hydroformylation reaction under predetermined temperature and pressure with the presence of the catalyst. The obtained aldehyde product is continuously withdrawn from the lower portion of the reactor 1 through the aldehyde product withdrawing line 15, as a liquid component.

On the other hand, the gaseous component in the reactor 1 is withdrawn to the gas/liquid separator 2 from the top portion of the reactor 1 through the line 17, and a gas/liquid separation is performed in the gas/liquid separator 2. The liquid phase component in the gas/liquid separator 2 is again returned to the reactor 1 through a liquid return line 18, and the gaseous component of gas phase is returned to the bottom portion of the reactor 1 through the recycled gas supply line 13.

The variation in the composition of the feed oxo gas can be compensated by an operational signal j from the feed forward control unit 82. This feed forward control is carried out based on equations (24) or (25) which is calculated by the mass balance around the reactor 1. The signal a of the concentration of CO in the oxo gas which is detected by the CO/oxo gas analysis meter 7, the signal c of the concentration of CO in the recycled gas which is detected by the CO/recycled gas analysis meter 5, and the signal b of the flow rate of the oxo gas which is detected by the oxo gas flow rate meter 6, are temporarily stored in a data memorizing unit 81, and are outputted to the feed forward control unit 82 from the data memorizing unit 81 as data e for the feed forward control. Based on the signal e, the feed forward control unit 82 calculates the feed forward operational signal j.

Further, the target value of the concentration of CO of the recycled gas which returns to the reactor 1, is set to perform desired production ratio of normal aldehyde and isoaldehyde. The control following the target value can be performed by controlling the degree of opening of the gas discharge control valve 9 or the feed oxo gas control valve 10, based on a feedback operational signal k.

The calculation of the feedback operation signal k is performed as follows. The signal c of the concentration of CO in the recycled gas which is detected by the CO/recycled gas analysis meter 5, is temporarily stored in the data memorizing unit 81. The feedback control unit 83 is inputted with this signal as the data f for the feedback control, at a constant period. The target value m of the partial pressure (concentration) of CO is memorized in the feedback control unit 83.

The calculation of the process gain $K_P$ is carried out as follows. The signal n of the discharged gas composition showing the component composition (CO and inert component) in the discharged gas which is transmitted from the discharged gas composition analysis meter 3, and the discharged gas flow rate signal d which is detected by the recycled gas discharge flow rate meter 4, are temporarily stored in the data memorizing unit 81.

The data h for calculating the process model is inputted to the model calculating unit 85 at a constant period, and unit 85 performs the calculation treatment of equation (16) or (23) based on the data and calculates the process gain. The calculated process gain is transmitted to the model 84 as an information i for changing the process model, which is used for changing the transfer function (equation (1)) of the process model. The feedback control unit 83 receives an information g of the process model from the model 84, and carries out the operational treatment based on equations (2) through (5). The discharge flow rate of the recycled gas or the flow rate of the feed oxo gas which minimizes a difference between a predicted concentration of CO and its target value m, can be provided as an operational quantity k for the feedback control by this calculation treatment.

The feed forward operational amount j and the feedback operational amount k respectively calculated as above, are added at the discharging flow rate controller 86 or the feed flow rate controller 87 and the added result is the set value thereof. The set value is transmitted to the recycled gas discharge control valve 9 or the feed gas control valve 10 as an operational signal l of the discharge flow rate or the feed flow rate for controlling the degree of opening. It is possible in place of this constitution to provide either one of the feed forward operational quantity j or the feedback operational quantity k to the discharge control valve as an operational amount.

EXAMPLE

A further detailed explanation will be given to the present invention by Examples and Comparative Examples as follows. However, this invention is not restricted to the following Examples so far as the gist thereof does not exceeds the scope of the invention.

Example 1

Figure 5:
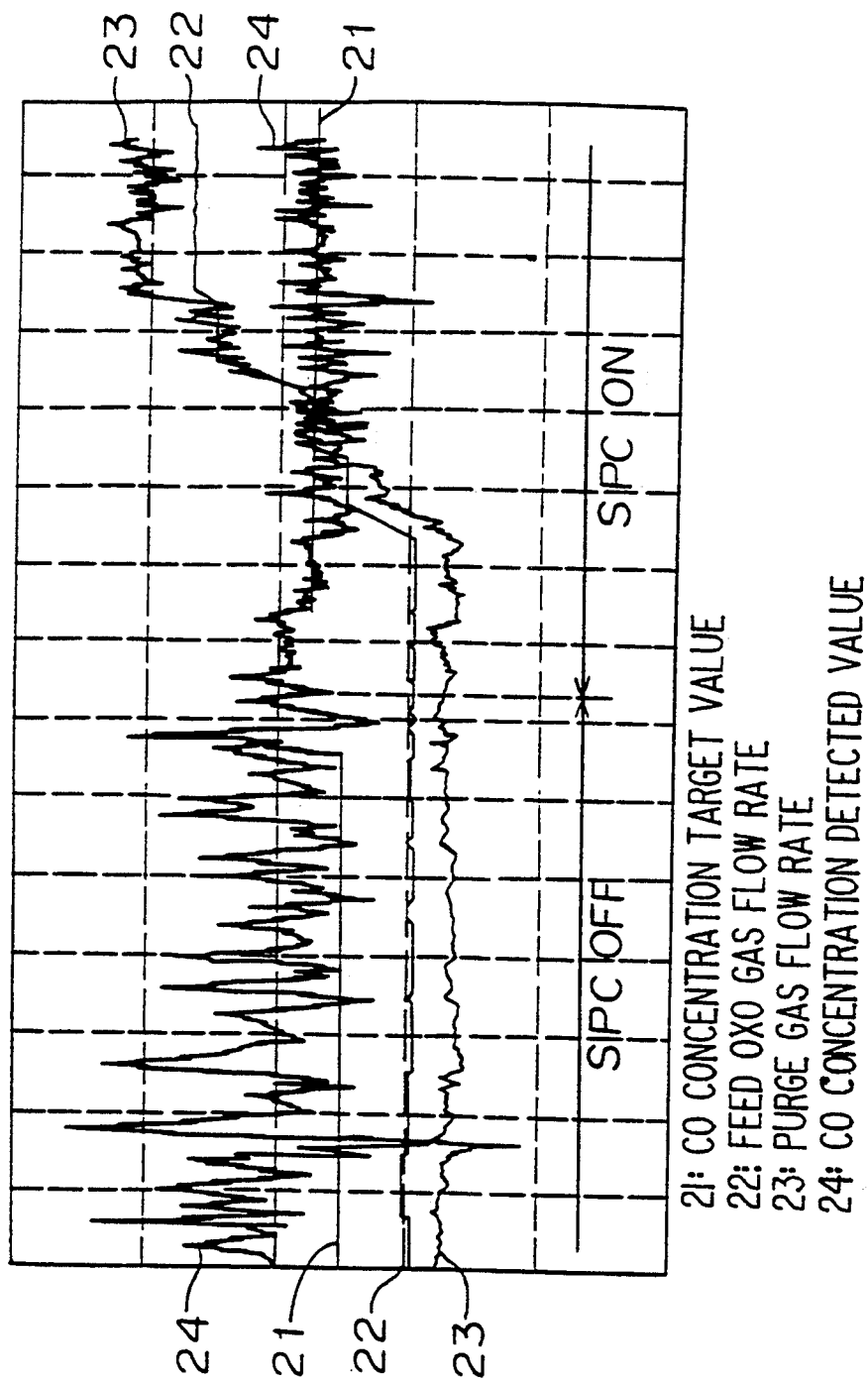
FIG. 5 is a graph showing a control result provided by the control methods of the first and the second embodiments of this invention.

A reaction control was performed under the construction of equipment of the system diagram shown in FIG. 1, and by the control method of hydroformylation reaction of the first embodiment. The behavior of the respective signals in the control is shown as "SPC OFF" on the left hand side of FIG. 5. In this control, the target value 21 of the concentration of CO and the feed oxo gas flow rate 22 were fixed to constant values. The discharging flow rate 23 and the detected value 24 of the concentration of CO in the recycled gas are respectively shown. The CO concentration 24 was well controlled in a predetermined range without particularly causing big variations.

Example 2

A reaction control was performed under the constitution of the system diagram shown in FIG. 3, and by the control method of hydroformylation reaction of the second embodiment. The result provided by the control is shown on the right hand side of FIG. 5 as "SPC ON". In this control, firstly, the target value 21 of the concentration of CO was changed, and successively, the feed oxo gas flow rate 22 was stepwisely changed. As a result, the discharging flow rate 23 well followed the change of the feed oxo gas flow rate 22, and the detected value 24 of the concentration of CO well converged into a predetermined range centering on the target value 21 of the concentration of CO.

Example 3

Figure 6:
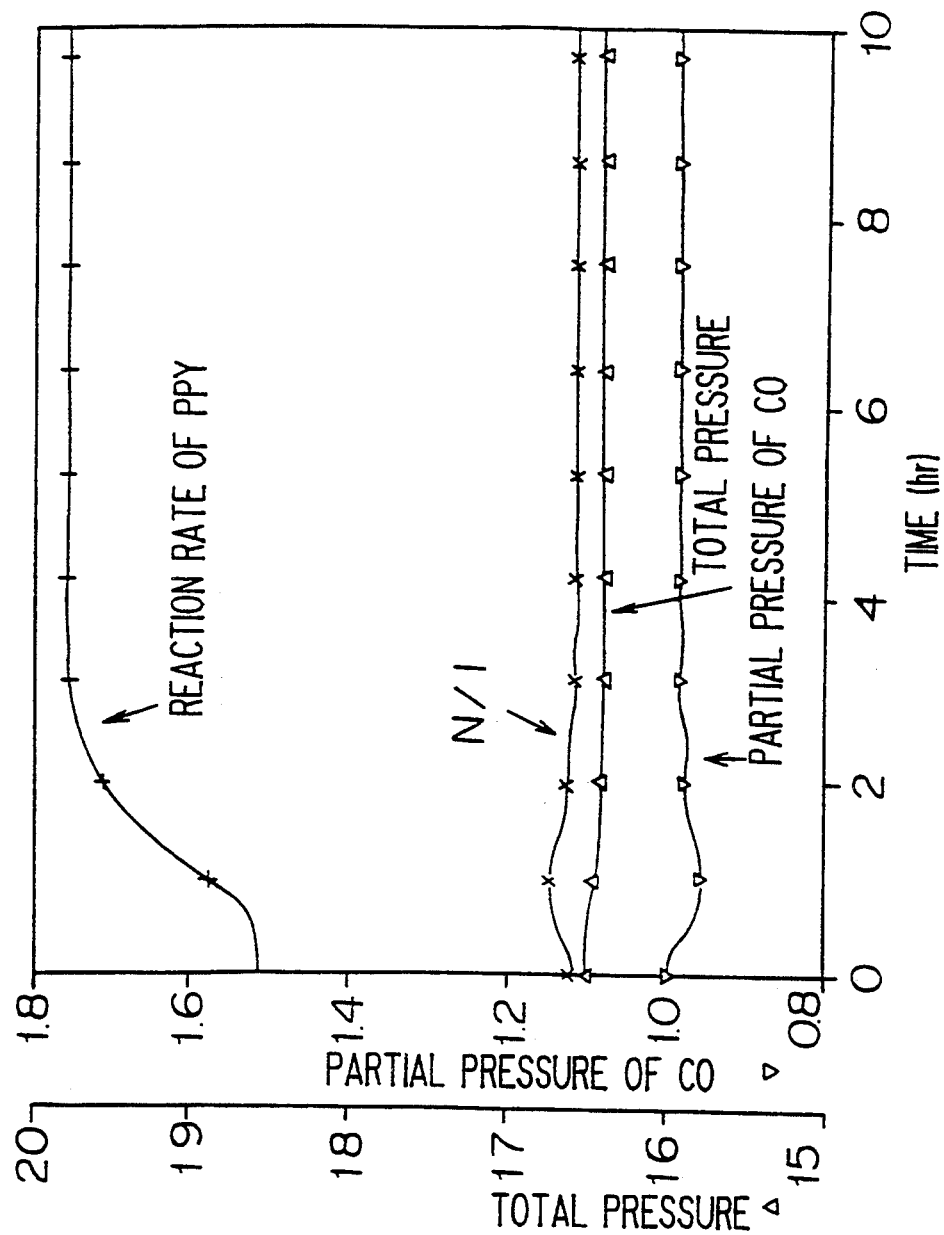
FIG. 6 is a graph showing a control result provided by the Example 3 of this invention.

An investigation was performed by a simulated calculation with respect to the controllability of reaction in case wherein the supply rate of propylene was increased by 10%, under the constitution of the system diagram shown in FIG. 1 and by using the control method of hydroformylation of the first embodiment. The supply quantity of propylene was increased by 10% which took one hour, while maintaining the pressure (total pressure) in the reactor to a predetermined pressure by controlling the supply quantity of the oxo gas, and the control of the concentration of CO in the reactor was performed by controlling the purging flow amount such that the CO concentration in the recycled gas was rendered to the target value. As a result, as shown in FIG. 6, the reaction rate of propylene (PPY), the ratio of n-butyl aldehyde/isobutyl aldehyde (N/I) obtained by the reaction, the pressure (total pressure) of the reactor, and the partial pressure of CO in the reactor were well controlled in predetermined ranges.

Example 4

Figure 7:
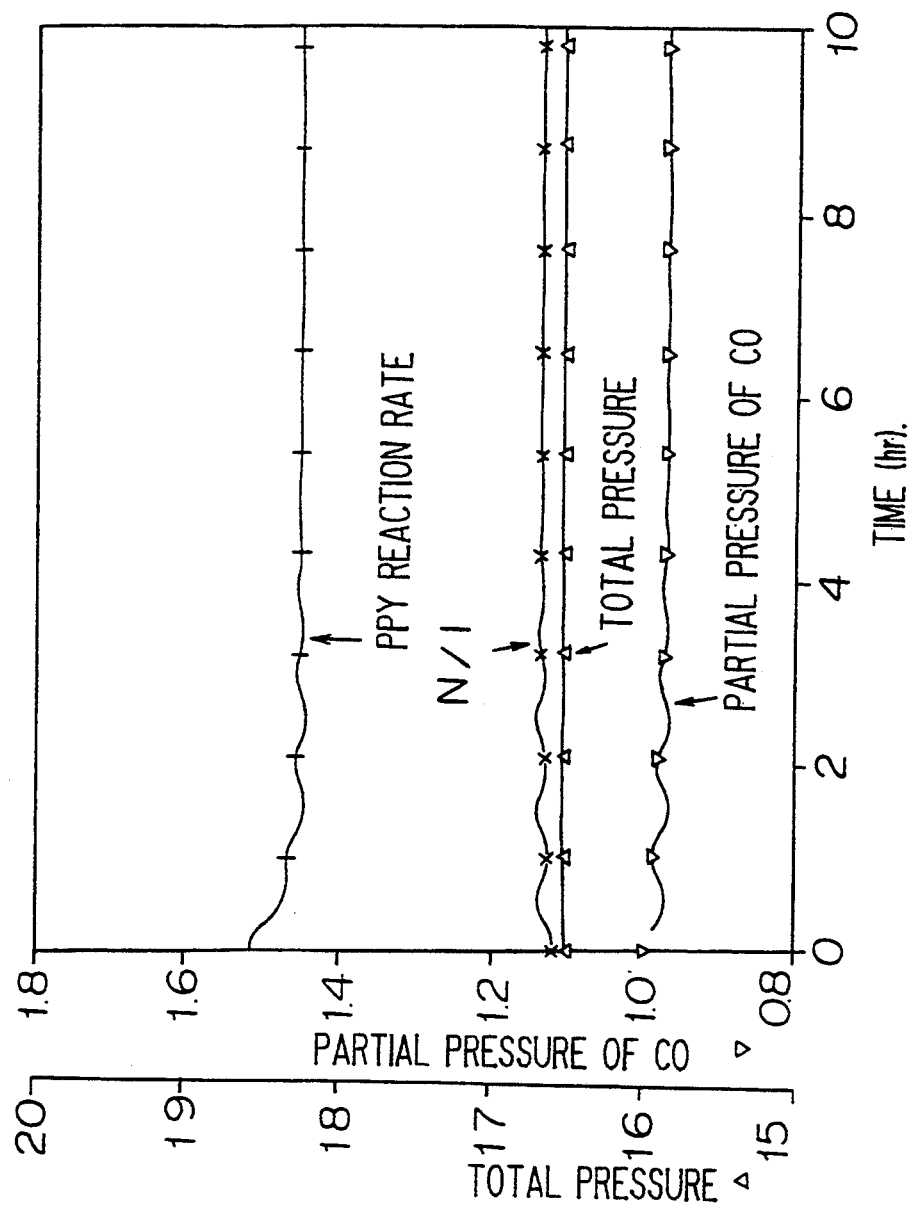
FIG. 7 is a graph showing a control result provided by the Example 4 of this invention.

An investigation was performed by a simulated calculation with respect to the controllability of reaction in case wherein the propane concentration in propylene was increased from 2.5% to 5%, under the constitution of the system diagram shown in FIG. 1, and by using the control method of a hydroformylation reaction of the first embodiment. The propane concentration in propylene was instantaneously increased from 2.5% to 5%, while maintaining the pressure (total pressure) in the reactor to a predetermined pressure by controlling the supply amount of the oxo gas, and the control of the concentration of CO in the reactor was performed by controlling the discharging flow rate such that the CO concentration in the recycled gas was rendered to its target value. As a result, as shown in FIG. 7, the reaction rate of propylene (PPY), the ratio of n-butyl aldehyde/isobutyl aldehyde (N/I) resulted by the reaction, the pressure (total pressure) of the reactor, and the partial pressure of CO in the reactor, were well controlled in predetermined ranges.

Example 5

Figure 8:
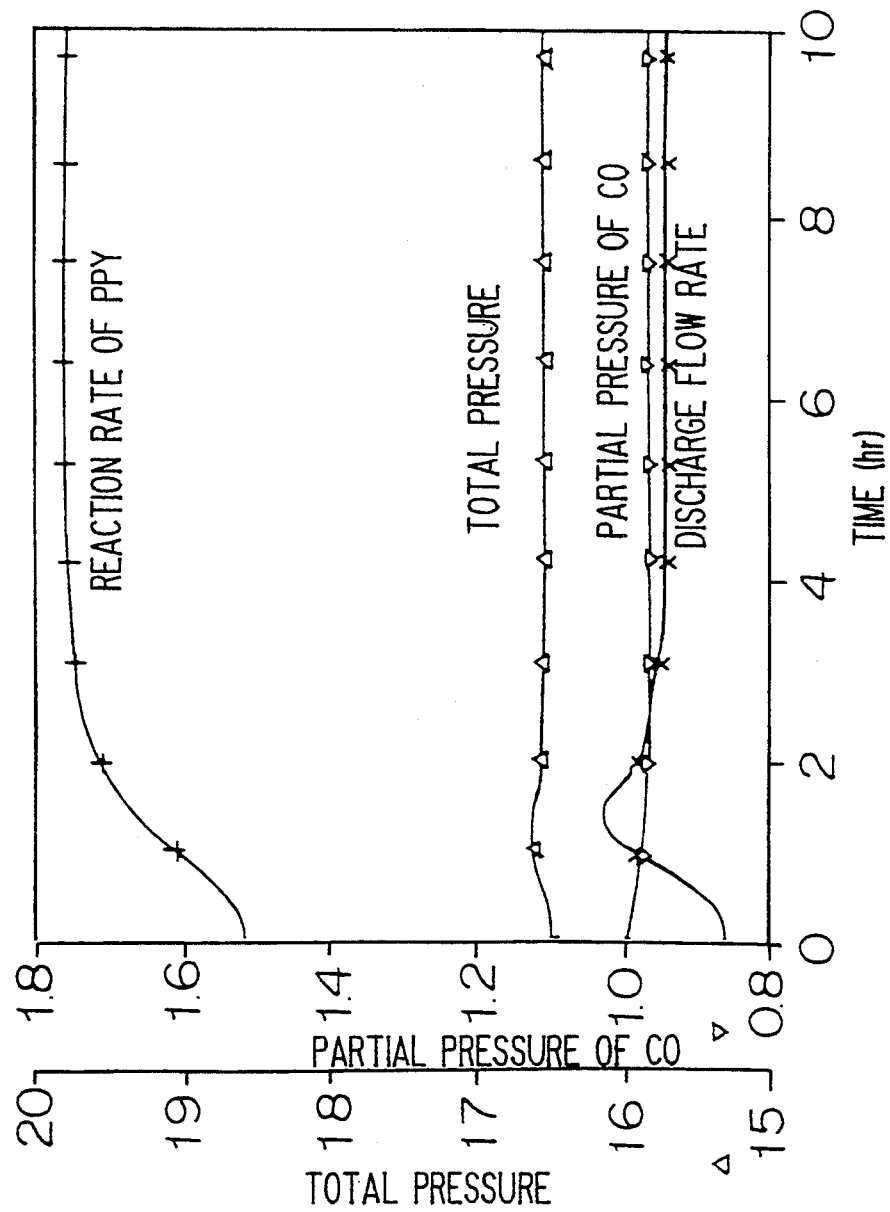
FIG. 8 is a graph showing a control result provided by the Example 5 of this invention.

An investigation was preformed by a simulated calculation on the controllability of reaction in case wherein the supply amount of propylene was increased by 10%, under the constitution of the system diagram shown in FIG. 1, and by using the method of controlling a hydroformylation reaction of the first embodiment. The supply rate of propylene was increased by 10% which took one hour, while maintaining the pressure (total pressure) in the reactor to a predetermined pressure by controlling the discharging flow rate, and the control of the CO concentration in the reactor was performed by controlling the supply rate of the oxo gas such that the CO concentration in the recycled gas was rendered to the target value. As a result, as shown in FIG. 8, the reaction rate of propylene (PPY), the pressure (total pressure) of the reactor, and the partial pressure of CO in the reactor were well controlled in predetermined ranges.

Example 6

An investigation was performed by a simulated calculation with respect to the controllability of reaction in case wherein the concentration of propane in propylene was increased from 2.5% to 5%, under the constitution of the system diagram shown in FIG. 1, and by using the control method of the hydroformylation reaction of the first embodiment. The propane concentration in propylene was instantaneously increased from 2.5% to 5%, while maintaining the pressure in the reactor to a predetermined pressure by controlling the discharging flow rate, and the control of the CO concentration in the reactor was performed by controlling the supply quantity of the oxo gas such that the CO concentration in the recycled gas was rendered to the target value.

Figure 9:
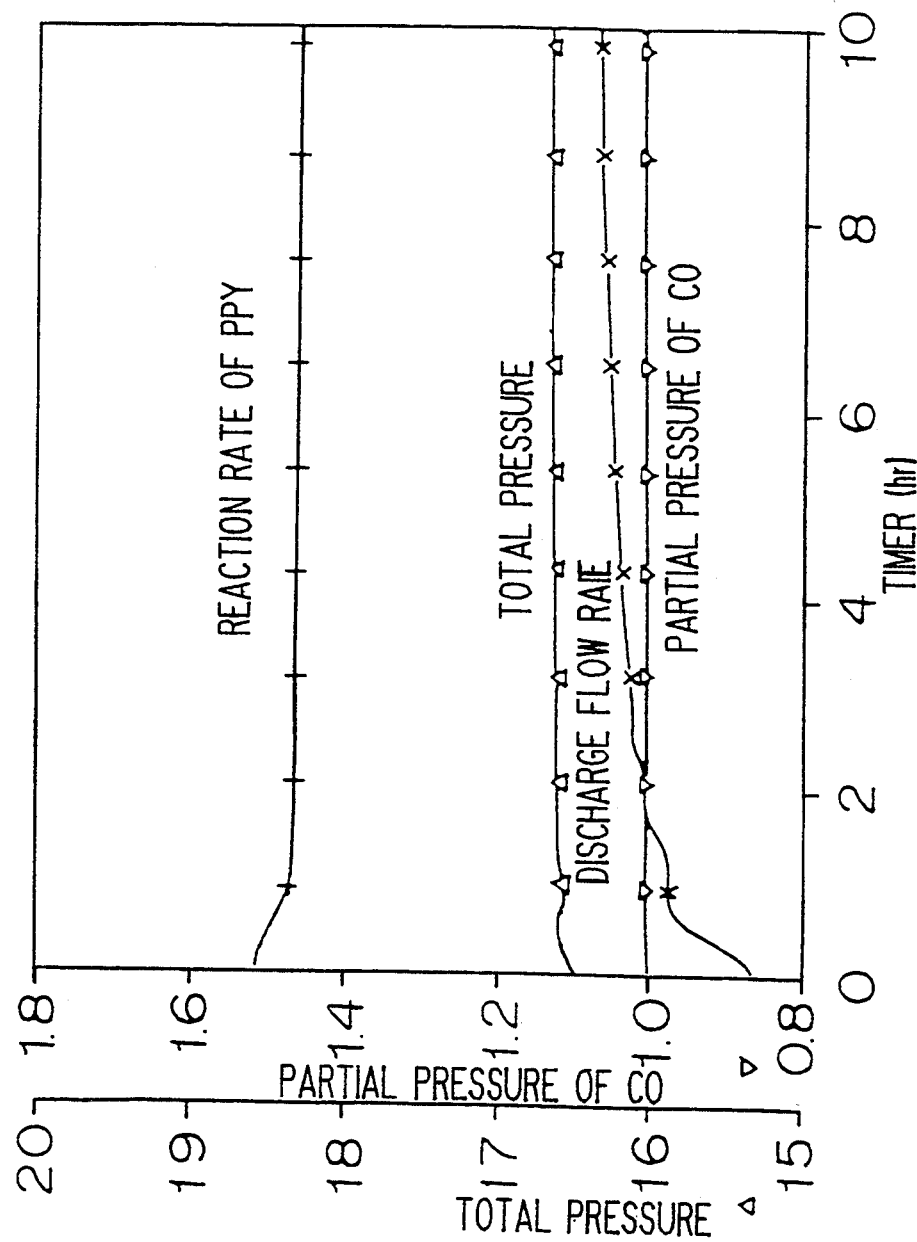
FIG. 9 is a graph showing a control result provided by the Example 6 of this invention.

As a result, as shown in FIG. 9, the reaction rate of propylene, the pressure (total pressure) of the reactor, and the CO partial pressure in the reactor were well controlled in predetermined ranges.

Comparative Example 1

Figure 10:
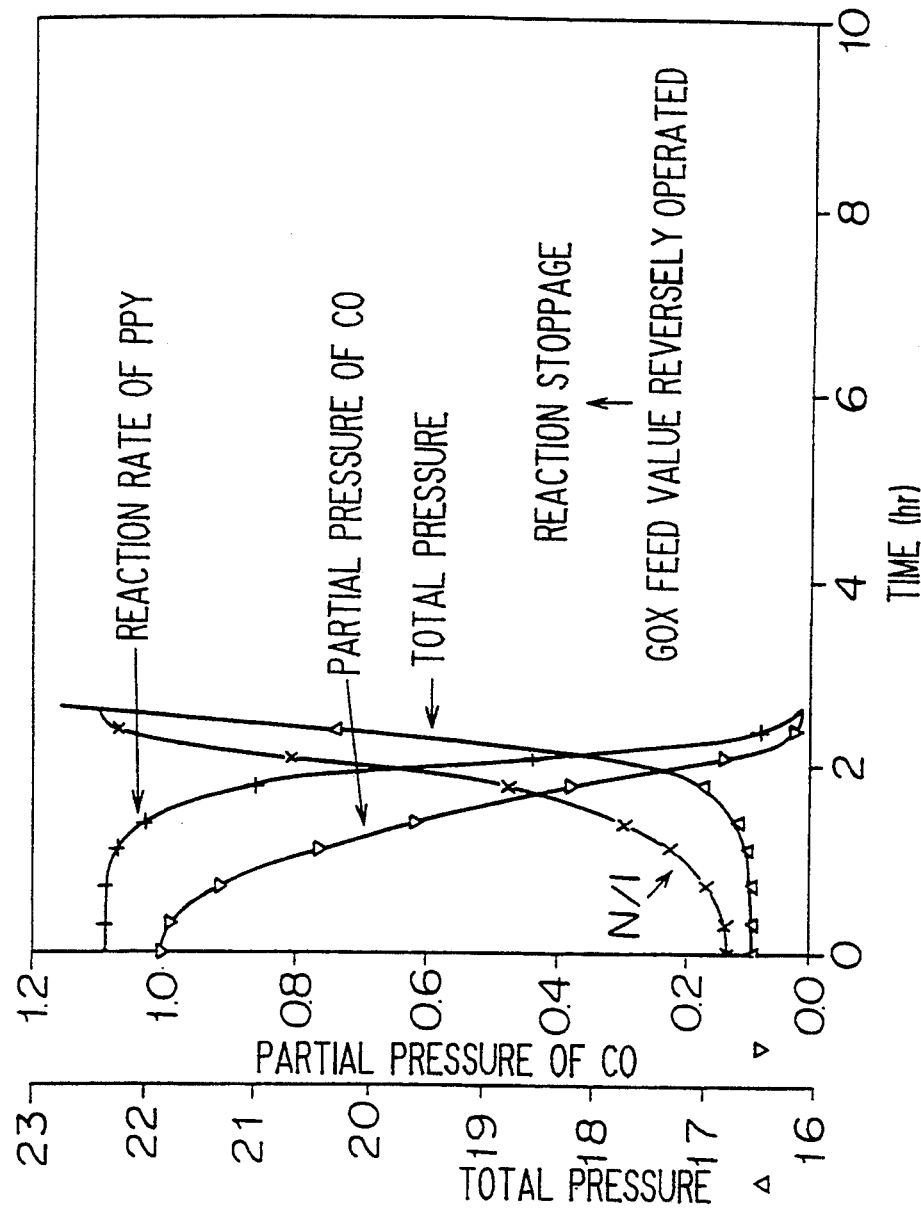
FIG. 10 is a graph showing a control result provided by the Comparative Example 1.

A control was performed similar to Example 3 except that the discharging flow rate was constant. The discharging flow rate was the same as an initial figure in Example 3. As a result, as shown in FIG. 10, the partial pressure of CO gradually decreased and the reaction stopped.

Comparative Example 2

Figure 11:
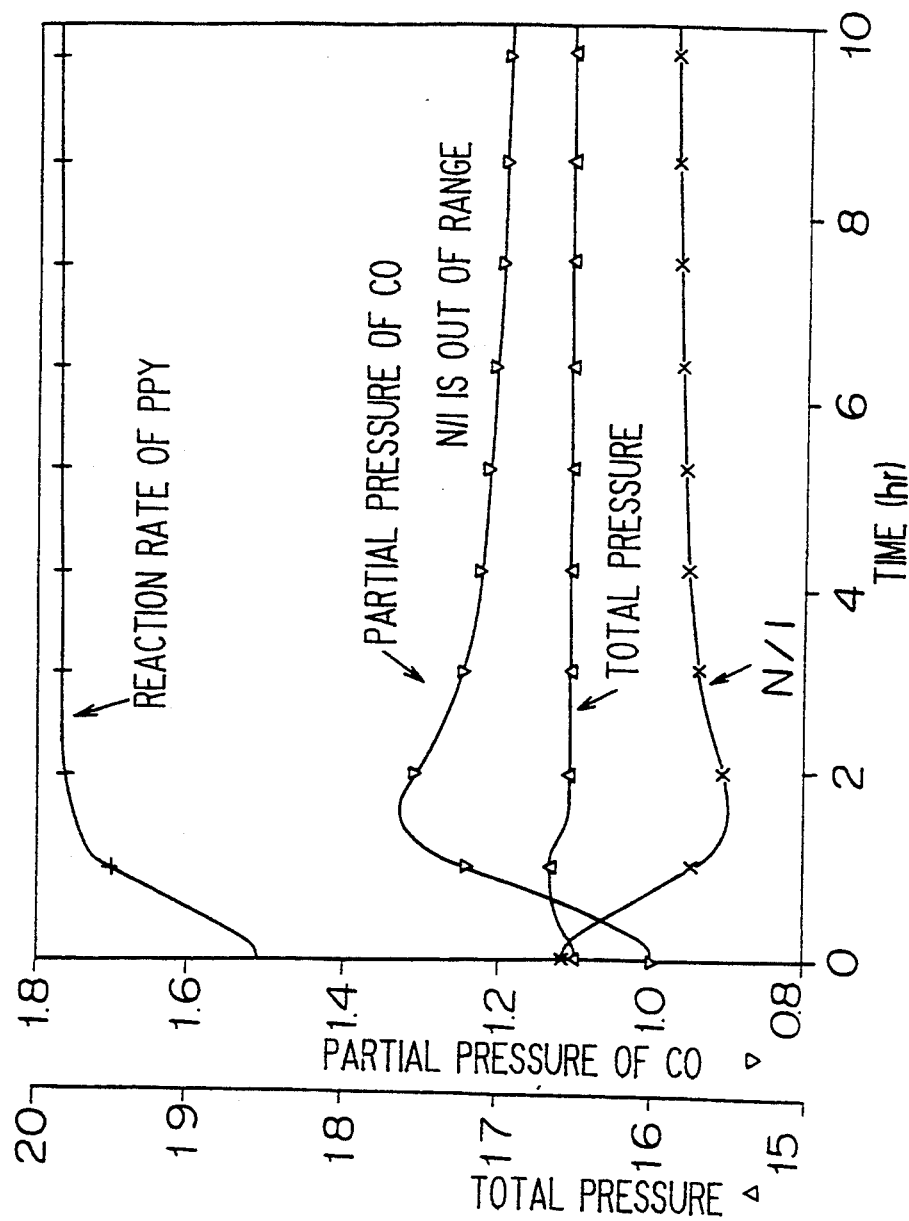
FIG. 11 is a graph showing a control result provided by the Comparative Example 2.

A control was performed similar to Example 5, except that the CO partial pressure in the reactor was not maintained to a predetermined pressure by controlling the feed oxo gas rate while supplying the oxo gas in correspondence to the supply quantity of propylene. As a result, as shown in FIG. 11, the CO partial pressure in the reactor could not converge to a range of a predetermined pressure, and therefore, the N/I ratio of butyl aldehyde provided by the reaction could not be maintained in a predetermined range.

Comparative Example 3

Figure 12:
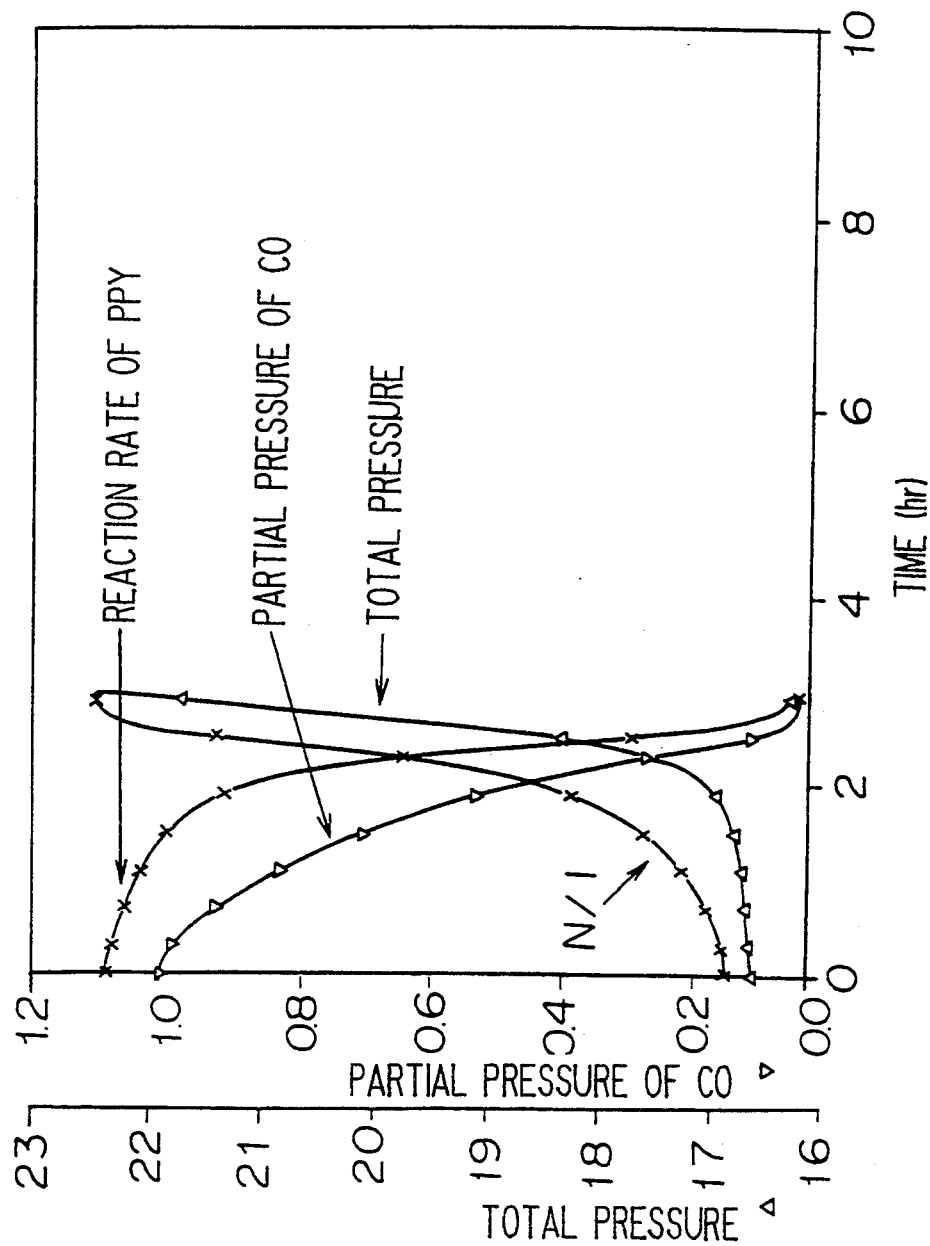
FIG. 12 is a graph showing a control result provided by the Comparative Example 3.

A control was performed similar to Example 4 except that the discharging was performed at a constant flow rate, and discharging flow rate was the same as on initial figure in Example 3, without controlling the discharging flow rate of the recycled gas. As a result, as shown in FIG. 12, with an increase in the partial pressure of propane in the reactor, the partial pressure of CO gradually decreased, the reaction rate of propylene decreased owing thereto, and the reaction stopped.

Comparative Example 4

Figure 13:
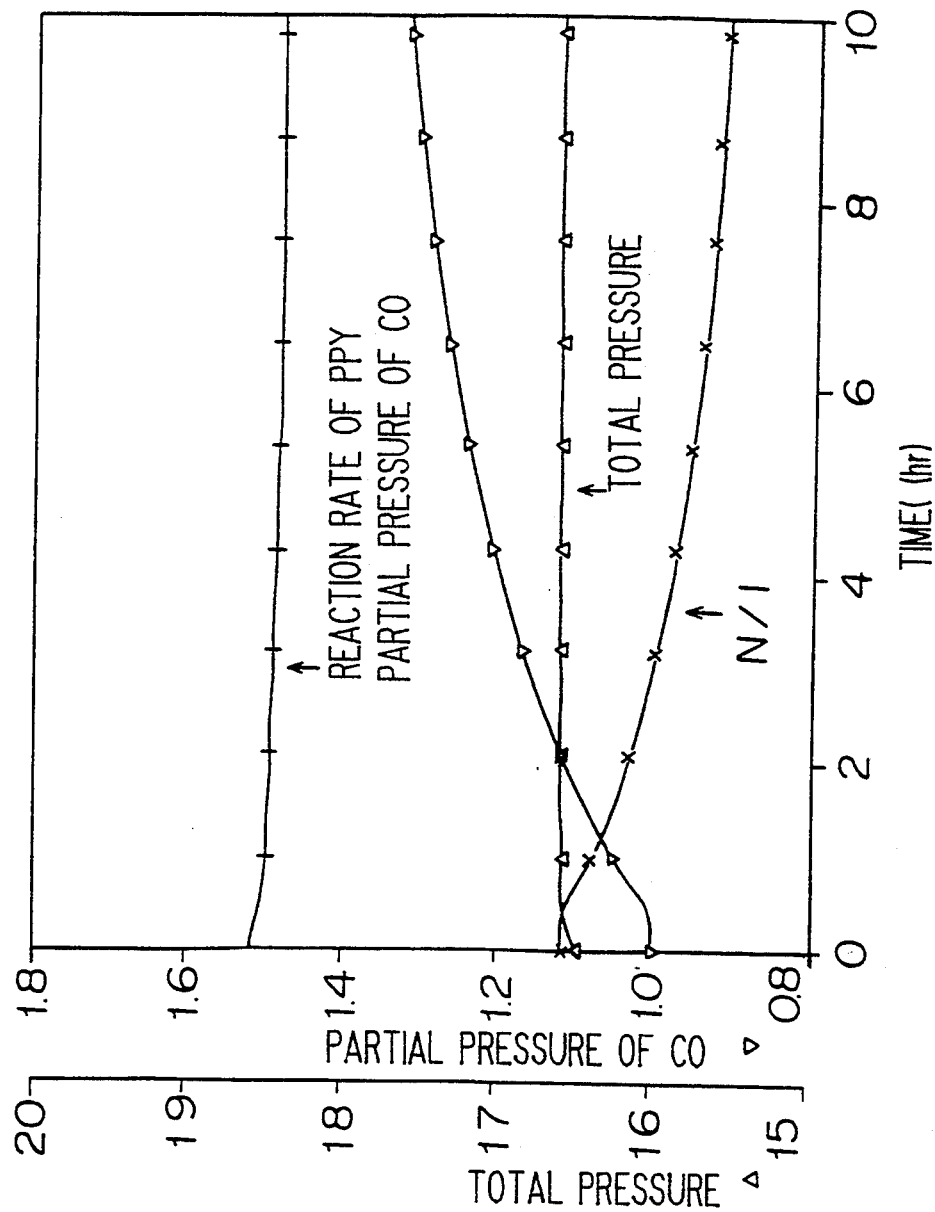
FIG. 13 is a graph showing a control result provided by the Comparative Example 4.

A control was performed similar to Example 6, except that the CO partial pressure in the reactor was not maintained to a predetermined pressure by controlling the feed oxo gas rate, while supplying the oxo gas in correspondence with the supply quantity of propylene. As a result, as shown in FIG. 13, the partial pressure of CO in the reactor gradually increased and could not converge into a predetermined range. Therefore, the N/I ratio of butyl aldehyde resulted by the reaction gradually decreased and could not be maintained in a predetermined range.

As stated above, according to the present invention, a constitution is adopted wherein the concentration of CO is controlled with a desired concentration of CO in the reaction system as a target value, by controlling a discharging flow rate of a recycled gas withdrawn from the reactor or a flow rate of the feed oxo gas which is fed to the reactor. Therefore, the concentration of CO in the reactor is not considerably fluctuated in the change of the target value of the concentration of CO, and the operation is performed by only setting the target value to the desired value, and the burden of an operator is alleviated.

Further, when a constitution is adopted wherein a model prediction control is performed by storing a process model having a predetermined transfer function in a computer, even in case wherein the change of the target value is especially rapidly performed, a stable control can be performed in correspondence with the change without a considerable fluctuation of control. Therefore, a stable process control is especially facilitated irrespective of an operator who performs the change.

When a construction is adopted wherein the coefficients of the above transfer function are successively changed by the data provided by the process, even in case wherein the production rate is considerably changed, a stable control can be continued in the process, without special operation by an operator.

Further, when a construction is adopted wherein a variation in the composition of the feed oxo gas is compensated by changing the discharging flow rate or the flow rate of the feed oxo gas based on a predetermined function, the concentration of CO in the reactor can easily be controlled in a desired range, irrespective of a considerable variation or difference in the composition of the feed oxo gas. Therefore, it is possible to perform the production of aldehyde in a desired ratio.

What is claimed is:

1. A method for producing aldehydes by subjecting an olefin, a feed oxo gas containing hydrogen and carbon monoxide, and a recycled gas withdrawn from a reactor and returned to the reactor, to a hydroformylation reaction in the reactor in the presence of a catalyst, which comprises the steps of:

providing an operation unit for adjusting a flow rate of the feed oxo gas supplied to the reactor or a flow rate of a discharged gas from the reactor;

setting out a target value for the partial pressure of carbon monoxide in the reaction system to obtain aldehydes with a desired production ratio of normal aldehyde to isoaldehyde;

detecting the partial pressure of carbon monoxide corresponding to the target value;

determining an operational amount of the operation unit required to maintain the detected partial pressure of carbon monoxide at the target value based on a deviation of the detected partial pressure of carbon monoxide from the target value; and adjusting the flow rate of the feed oxo gas or the flow rate of the discharged gas based on the operational amount.

2. The method for producing aldehydes according to claim 1, wherein detecting the partial pressure of carbon monoxide is performed by detecting the partial pressure of carbon monoxide in the recycled gas which is returned to the reactor.

3. The method for producing aldehydes according to claim 1, wherein detecting the partial pressure of carbon monoxide is performed by detecting the partial pressure of carbon monoxide of the oxo gas which is formed by joining the recycled gas to be returned to the reactor and a feed oxo gas to be supplied to the reactor.

4. The method for producing aldehydes according to claim 1 further comprising:

storing in a computer a process model for simulating the hydroformylation reaction which is provided with a predetermined signal transfer function having an input of the operational amount to adjust the flow rate of the discharged gas or the feed oxo gas and an output of a calculated value of the partial pressure of carbon monoxide;

providing the process model with the input by successively selecting an input series comprising a plurality of inputs which are successively generated at every predetermined cycle;

successively calculating a future output series based on the output of the process model;

selecting an output series among the calculated future output series wherein a difference between the future output series and the predetermined future target value is small; and setting out the operational amount based on the input series corresponding to the selected one of the output series.

5. The method for producing aldehydes according to claim 4, wherein selecting the one of the output series is performed in accordance with the method of least squares.

6. The method for producing aldehydes according to claim 4, wherein the transfer function is expressed by the following equation (1):

$$G(s) = \{K_p/(1+T_p \cdot s)\} \cdot \exp(-T_L \cdot s) \quad (1)$$

where $K_p$ is a process gain, $T_p$, a time constant, $T_L$, a dead time and s, a Laplacian operator.

7. The method for producing aldehydes according to claim 4, wherein coefficients of the signal transfer function are calculated by detecting signals relating to a flow rate and a composition of the discharged gas and based on at least the signals relating to a flow rate and a composition of the discharged gas.

8. The method for producing aldehydes according to claim 7, wherein the process gain $K_p$ which is the coefficient of the signal transfer function is calculated in accordance with the following equation (16):

$$K_p = A_i \cdot A_{co}/F_t \qquad (16)$$

where $A_i$ is a concentration of an inert component in the discharged gas, $A_{co}$, a concentration of CO and $F_t$, a total discharging rate.

9. The method for producing aldehydes according to claim 7, wherein the process gain $K_p$ which, is the coefficient of the signal transfer function is calculated in accordance with the following equation (23):

$$K_p = (1 - 2A_{co})/2F_t \qquad (23)$$

where $A_{co}$ is a concentration of CO in the discharged gas and $F_t$, a total discharging rate.

10. The method for producing aldehydes according to claim 1, wherein the operational amount is determined by further detecting signals relating to a flow rate and a composition of the feed oxo gas and further based on the signals relating to a flow rate and a composition of the feed oxo gas.

11. The method for producing aldehydes according to claim 10, wherein the operational amount to adjust the flow rate of the discharged gas is determined based on the following equation (24):

$$du/dt = (F_{in}/C_{co}) \cdot dB_{co}/dt \qquad (24)$$

where u is a discharged flow rate, $F_{in}$, a feed oxo gas flow rate, $C_{co}$, the partial pressure of CO in the recycled gas and $B_{co}$, the partial pressure of CO in the feed oxo gas.

12. The method for producing aldehydes according to claim 10, wherein the operational amount to adjust the flow rate of the feed oxo gas is determined based on the following equation (25):

$$dF_{in}/dt = -(F_{in}/B_{co}) \cdot dB_{co}/dt \qquad (25)$$

where $F_{in}$ is a feed oxo gas flow rate and $B_{co}$, the partial pressure of CO in the feed oxo gas.

13. The method for producing aldehydes according to claim 1 or claim 4, wherein adjusting the flow rate of the discharged gas or the feed oxo gas is performed by PID-controlling a degree of opening of the discharged gas or the feed oxo gas control valve based on the operational amount.

14. The method for producing aldehydes according to claim 1, wherein the olefin is selected from the group consisting of ethylene, propylene, butene, butadiene, pentene, hexene, hexadiene, octene, octadiene, decene, hexadecene and octadecene.

15. The method for producing aldehydes according to claim 1, wherein the olefin is propylene.

16. The method for producing aldehydes according to claim 1, wherein the catalyst is a Group VIII metal complex.

17. The method for producing aldehydes according to claim 1, wherein the reaction temperature of the hydroformylation reaction is in a range of 50° through 150° C.

18. The method for producing aldehydes according to claim 1, wherein the reaction pressure of the hydroformylation reaction is in a range of 5 through 100 atm.

19. The method for producing aldehydes according to claim 1, wherein the molar ratio of hydrogen to carbon monoxide ($H_2/CO$) in the reactor is in a range of 1/1 through 6/1.

20. The method for producing aldehydes according to claim 1, wherein the reaction system of the hydroformylation reaction is a continuous system performed in an agitation type reacting vessel.

* * * * *